United States Patent [19]

Bull et al.

[11] Patent Number: 5,506,145
[45] Date of Patent: Apr. 9, 1996

[54] DETERMINATION OF AN INDIVIDUAL'S INFLAMMATION INDEX FROM WHOLE BLOOD FIBRINOGEN AND HEMATOCRIT OR HEMOGLOBIN MEASUREMENTS

[76] Inventors: Brian S. Bull, 24489 Barton Rd., Loma Linda, Calif. 92354; Robert A. Levine, 31 Pilgrim La., Guilford, Conn. 06437; Stephen C. Wardlaw, 191 N. Cove Rd., Old Saybrook, Conn. 06475

[21] Appl. No.: 348,345

[22] Filed: Dec. 2, 1994

[51] Int. Cl.⁶ ............................ G01N 33/86; G01N 33/72
[52] U.S. Cl. ........................... 436/69; 436/66; 436/70; 435/2; 435/13; 210/782; 73/61.41; 73/61.43; 73/61.63
[58] Field of Search ..................... 436/63, 66, 69, 436/70; 73/61.41, 61.43, 61.63; 210/782; 435/2, 13

[56] References Cited

U.S. PATENT DOCUMENTS

| | | | |
|---|---|---|---|
| 4,156,570 | 5/1979 | Wardlaw | 356/36 |
| 4,558,947 | 12/1985 | Wardlaw | 356/39 |
| 4,683,579 | 7/1987 | Wardlaw | 377/11 |
| 4,843,869 | 7/1989 | Levine et al. | 73/61.43 |
| 4,875,364 | 10/1989 | Levine et al. | 73/61.72 |
| 4,953,975 | 9/1990 | Levine et al. | 356/246 |
| 5,132,087 | 7/1992 | Manion et al. | 422/58 |
| 5,137,832 | 8/1992 | Levine et al. | 436/69 |

OTHER PUBLICATIONS

Bull et al. *The Lancet*, Aug. 16, 1986, pp. 377–380.
Bull et al. *The Lancet*, Oct. 21, 1989, pp. 965–967.
Reibnegger et al. *The Lancet*, vol. 339, Jun. 6, 1992, pp. 1394–1397.

*Primary Examiner*—Jill Warden
*Assistant Examiner*—Maureen M. Wallenhorst
*Attorney, Agent, or Firm*—William W. Jones

[57] ABSTRACT

Useful information about a subject's level of systemic inflammation is obtained by quantitatively measuring the amount of fibrinogen and the hematocrit and or hemoglobin in the subject's whole blood. The fibrinogen measurement, when combined with an hematocrit or hemoglobin measurement, provides a systemic Inflammation Index value for the donor. The method is not affected by blood variables which are not related to the presence of inflammation, which blood variables are known to invalidate an erythrocyte sedimentation rate, which is the most frequently used blood test for detecting systemic inflammation in humans.

6 Claims, 1 Drawing Sheet

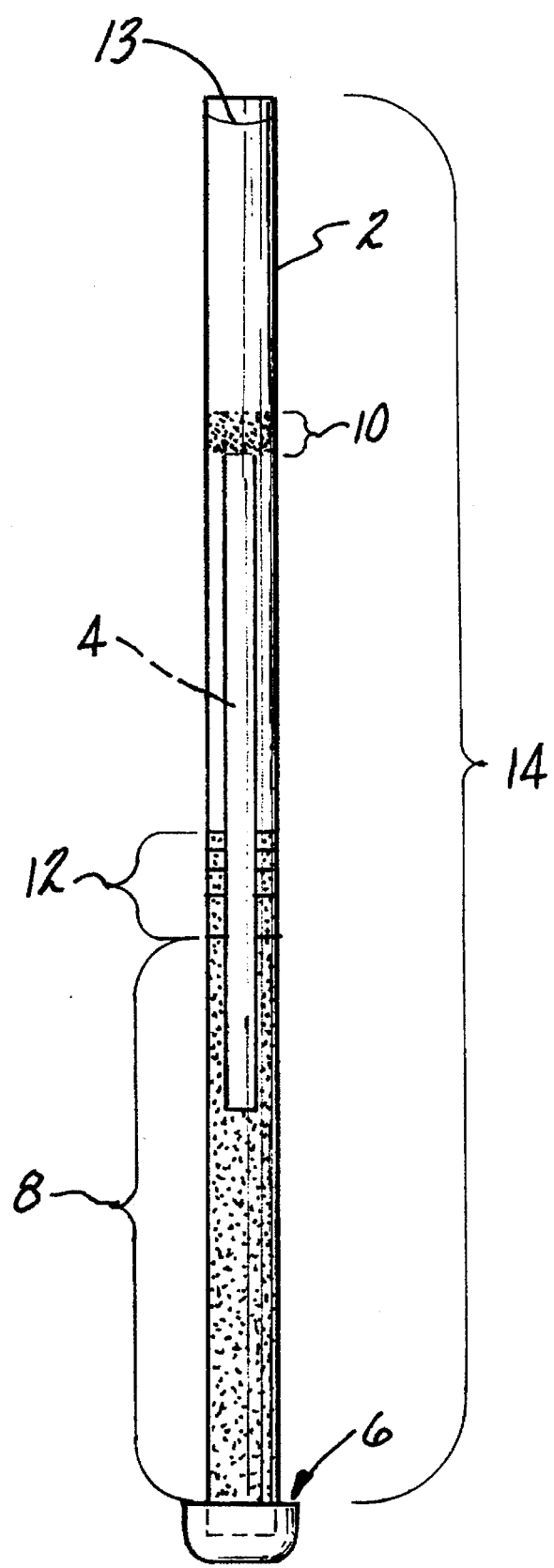

DETERMINATION OF AN INDIVIDUAL'S INFLAMMATION INDEX FROM WHOLE BLOOD FIBRINOGEN AND HEMATOCRIT OR HEMOGLOBIN MEASUREMENTS

TECHNICAL FIELD

This invention relates to a method for determining the presence or absence of an inflammatory condition in an individual by quantifying both the fibrinogen content and the hematocrit or hemoglobin in a sample of the individual's blood, and calculating a composite Inflammation Index for the individual which is derived from the aforesaid two variables.

BACKGROUND ART

Inflammation is a basic pathophysiologic process that is defined as the reaction of vascularized living tissue to local injury. The inflammatory process is important to the host because it serves in the process of repair of the injury and destruction of pathogenic organisms and tumors but sometimes inflammation may be harmful when it continues unchecked, as in rheumatoid arthritis. The detection of the inflammatory process is important to physicians because it indicates the presence of significant illness or injury. Examples of illnesses often characterized by significant inflammation are myocardial infarction, active tuberculosis, osteomyelitis (bone infection), rheumatoid arthritis, cholecytistis (infected gall bladder), and pyelonephritis (infected kidney), and disseminated cancer among others.

Patients who have significant inflammatory processes often have signs and symptoms of inflammation that are well known, such as fever, fatigue, loss of appetite, low blood pressure, and sometimes abnormalities in the amount of circulating white blood cells including both elevation and depression of their numbers, but these signs and symptoms are neither sensitive nor specific to the presence of inflammation. Many diseases and physical conditions, such as those listed above will cause inflammatory responses which can be noted in the blood. These inflammatory responses can frequently occur before more specific signs and symptoms of disease can be identified, and thus the detection of the presence of inflammation may allow more prompt diagnosis and treatment of the underlying condition. The best known and most widely used blood test indicator of inflammation is the erythrocyte sedimentation rate or ESR. The ESR was discovered by Fahraeus and popularized and improved by Wintrobe and Westergren. The Westergren erythrocyte sedimentation rate, or Westergren ESR, or WESR, which is sensitive to global elevations in inflammatory proteins is performed by measuring the distance the erythrocytes have sedimented in 60 minutes in a sample of anticoagulated blood which has been placed in a 200 mm long tube of defined dimensions. It has been an enduring laboratory test for both screening patients on an initial visit to a physician, and for following the evolution of the inflammatory condition in return visits. Despite the widespread use of the ESR procedure, there are certain drawbacks to this test which relate to, among other things, the amount of blood used to perform the test (at least one milliliter, which is a large amount for an infant); the amount of time needed to perform the test (one hour), and the fact that the test should optimally be performed within two hours of obtaining the blood. The ESR performed in the manner described by Wintrobe and Westergren is also affected by factors that may not indicate the presence or absence of inflammation such as: the presence of abnormally shaped red cells; the presence of proteins affecting the viscosity of the blood; the presence of antibody or cold agglutinens directed against red blood cells; the general level of gamma globulins even if they are not directed against the red cells; and deviations from verticality of the ESR tube while the test is being performed, as well as ambient temperature and vibration. Physicians therefore have attempted to develop other tests for inflammation that may be easier or quicker, or more sensitive or specific. Such tests include the C reactive protein or CRP; the white blood cell count; the granulocyte count (a component of the white blood cell count); the orosomucoid protein; the hematocrit or hemoglobin; and the fibrinogen. A total of at least sixteen tests have been used to monitor inflammation. All of these tests have advantages, as well as disadvantages, but none of them have been shown to be superior to the ESR.

It would be highly desirable to have a procedure for ascertaining the level of systemic inflammation; and which procedure requires only a small sample of blood; and which procedure can be relatively quickly performed or which procedure may be performed after a period of several hours if necessary; and which procedure is not adversely affected by abnormal blood conditions that skew the results of the ESR.

DISCLOSURE OF THE INVENTION

A technique exists for the ranking of the utility of laboratory tests called "consensus analysis". This technique, conceived by Bull and others based in part on the work of Spearman, and modernized by Bull, is able to discern the most effective test, or most effective weighted combination of tests, to detect a given condition. The technique of "concensus analysis" is described in an article by Bull et al entitled "Ranking of Laboratory Tests by Consensus Analysis", published Aug. 16, 1986 in *The Lancet*. Using consensus analysis, the ESR has proven itself the best single performer among the sixteen tests now used to monitor rheumatology patients. Since a major contributor to the ESR is known to be the fibrinogen level, and the hematocrit or hemoglobin are known to be decreased in inflammatory conditions, we have applied consensus analysis to ascertain if these determinations, which may be performed more rapidly and on smaller volumes of blood, would, if combined in a composite, yield information clinically equivalent to, or better than that provided by the widely used ESR.

We have found, using the tools of consensus analysis, and the results of analyses of blood samples taken from a group of one hundred patients who had demonstrated a wide range of indicators of inflammation, that a combination of the WESR, fibrinogen and the CRP, which combination we have dubbed "the composite index", was the best indicator of the presence of systemic patient inflammation.

Because the composite index consists of tests that cannot be easily or rapidly performed, it does not possess significant clinical utility We found, however, that a composite result procedure involving fibrinogen measurements and hematocrit or hemoglobin measurements (the "Inflammation Index") provides information about the extent of inflammation which closely conforms to the results from the composite index, and is in closer conformity to the composite index results than are the results obtained from the WESR alone.

The Inflammation Index, in humans, using the fibrinogen measurement expressed in mg/dl, and the hematocrit (Hct) measurement as a volume percent of the packed red cells in the blood sample, was determined by us to be equal to:

0.154 (fibrinogen)−1.667(Hct)+42.

For example, a patient without significant clinical inflammation and a fibrinogen level of 200 mg/dl with an hematocrit of 42% would result in an Inflammation Index as follows:

0.154(200)−1.667(42.0)+42≈3

A patient with a high level of systemic inflammation and a fibrinogen level of 800 mg/dl with an hematocrit of 28.0% would result in an Inflammation Index as follows:

0.154(800)−1.667(28.0)+42≈118

If hemoglobin values are used, expressed in gm/dl the constant −1.667 will be −5.001. The other constants will remain the same.

Thus the general equation for determining a donor's inflammation index is: I=a(f)+b(h)+c; wherein "I" is the inflammation index; "f" is the fibrinogen level in the blood sample; "h" is the hematocrit or hemoglobin value in the blood sample; and "a", "b", and "c" are empirically derived constants.

For human blood, the empirical constants were derived by comparing the consensus analysis of human blood ESR analysis, human blood fibrinogen analysis, and human blood CRP analysis from a donor population of 100 patients displaying a wide range of inflammation indicators, with the fibrinogen/fibrin level and a hematocrit or hemoglobin determination combination from the same donor population.

If a non-human mammalian blood sample, as for example animal blood, were being analyzed, then different constants would be required, and a parallel consensus analysis determination would have to be made to determine such constants.

It should be noted that the Inflammation Index value, being a composite number, has no dimensions or units, and that the range of values resulting from the test is similar to the range of values of the WESR. The Inflammation Index results obtained by performing the method of this invention can therefore be easily interpreted by physicians with the numerical result being approximately comparable to a WESR without being adversely affected by the factors previously mentioned and with the added reliability inherent in the composite number.

A simple and quick procedure for quantifying the fibrinogen content in an anticoagulated whole blood sample is described in U.S. Pat. No. 5,137,832, granted Aug. 11, 1992 to R. A. Levine et al. The aforesaid procedure may be performed in a physician's office in a matter of about fifteen minutes, or so. The paraphernalia used to perform the aforesaid fibrinogen quantification includes a blood sampling tube of precise volume, and a float which is positioned in the tube. A layer of precipitated fibrinogen and/or fibrin settles on the top of the float after centrifugation of the sample in the tube. A computerized instrument which measures the linear length of the fibrinogen and/or fibrin layer in the tube as well as the length of the total sample in the tube, is used to convert the fibrinogen linear layer measurement to a quantification of the amount of fibrinogen and/or fibrin in the sample. The same paraphernalia can also be used to measure a patient's hematocrit and hemoglobin as described in U.S. Pat. No. 4,843,869, granted Jul. 4, 1989 to R. A. Levine et al. By combining fibrinogen level information with information about the hematocrit or hemoglobin level in the blood, as described above, one can derive an Inflammation Index value for the patient The fibrinogen-hematocrit or hemoglobin values, and thus the Inflammation Index value, can be determined much more rapidly than the WESR and/or the CRP and the amount of blood required to perform the method is about one-tenth that needed for the WESR. In addition, and most importantly, the results will not be skewed by systemic abnormalities that render the WESR inaccurate.

It is therefore an object of this invention to provide a procedure for providing an Inflammation Index value for a blood sample, which index is indicative of systemic inflammation in the donor of the blood sample.

It is a further object of this invention to provide a procedure of the character described which is not susceptible to systemic abnormalities that render the WESR unreliable.

It is an additional object of this invention to provide a procedure of the character described wherein the level of fibrinogen and/or fibrin is quantified, and is combined with an hematocrit or hemoglobin quantification in the blood sample in order to ascertain a measure of systemic inflammation.

It is yet another object of this invention to provide a procedure of the character described wherein the amount of blood needed for the procedure is small and the time needed to perform the procedure is short.

BRIEF DESCRIPTION OF THE DRAWING

These and other ojects and advantages will become more readily apparent form the following detailed description of an embodiment of the invention when considered in connection with the accompanying drawing which is a side elevational view of a blood sampling tube used to perform the procedure of this invention.

SPECIFIC EMBODIMENT OF THE INVENTION

Referring now to FIG. 1, there is shown a blood sampling tube which is denoted generally by the numeral 2. The tube 2 is typically a capillary tube and it contains an elongated plastic insert or float 4 which is formed from a plastic which has a specific gravity that results in the insert 4 settling into and floating on a layer 8 of packed red blood cells 8 that settle into the bottom of the tube 2 when the tube 2 and insert 4 are centrifuged with a sample of anticoagulated whole blood contained in the tube 2. The bottom of the tube 2 is closed with a plastic cap 6 or the like. When the tube 2, insert 4 and blood sample are processed as described in the aforesaid U.S. Pat. No. 5,137,832, the specification of which is incorporated herein in its entirety for purposes of enablement, and centrifuged, the blood sample constituents will settle out in different layers as shown in the drawing. The red cells will settle into the lowermost portion of the tube 2 in a layer 8. The insert 4 will settle into the red cell layer 8 and float therein. The insert 4 will project upwardly through the white cell/platelet, or buffy coat layer 12 into the plasma layer, which is the uppermost layer of the sample. The precipitated fibrinogen and/or fibrin in the blood sample will settle into a band 10 which ends up on the top of the insert 4 and in the plasma layer. The length of the red cell layer 8 is measured by a preprogrammed microprocessor-operated instrument such as those disclosed in U.S. Pat. Nos. 4,156,570, granted May 29, 1979; 4,558,947, granted Dec. 17, 1985; and 4,683,579, granted Jul. 28, 1987, all to S. C. Wardlaw. Instruments of the type disclosed in the latter two patents are sold by Becton Dickinson and Company under the trademark QBC AUTOREADER®. The red blood cell layer measurement along with a measurement of the length of entire blood sample 14 as taken from the miniscus 13 at the top of the plasma layer to the closure cap 6 will provide the hematocrit value for the blood sample. When calculating the hematocrit, the instrument will correct for the fact that the insert extends a short distance into the red cell layer 8. The instrument is also used to measure the linear extent of the fibrinogen/fibrin layer 10 and convert that measurement into a fibrinogen count. The instrument will then use the hematocrit value and the fibrinogen/fibrin value to calculate the Inflammation Index by making the calculation specified above. When the Inflammation Index has been determined, its value will be displayed or printed out by the instrument for the physician.

It will be readily appreciated that the determination of systemic inflammation by using the procedure of this invention can be performed with a minimal amount of blood, and in a minimum amount of time. The procedure of this invention is essentially immune to factors, both biological and procedural, which will produce inaccurate results when using the WESR procedure to determine the extent of systemic inflammation. While the aforesaid description of the invention has been specifically directed to the determination of an Inflammation Index for humans, the invention can also be used to determine an Inflammation Index for other mammalian species, and thus can be used in the measurement of inflammation in animals in the practice of veterinary medicine. Naturally, different multipliers of the hematocrit and fibrinogen/fibrin measurements and different constants will have to be determined for different animal species.

Since many changes and variations in the disclosed embodiments of the invention may be made without departing from the inventive concept, it is not intended to limit the invention otherwise than as required by the appended claims.

What is claimed is:

1. A method for determining the degree of mammalian donor systemic inflammation from a sample of donor anticoagulated whole blood, said method comprising the steps of:

a) providing a transparent tube containing an elongated float;

b) drawing a sample of donor anticoagulated whole blood into said tube;

c) centrifuging the sample of whole blood in the tube;

d) measuring the amount of fibrinogen/fibrin in said blood sample in the tube;

e) determining a hematocrit or hemoglobin value for the blood sample in the tube;

f) computing a number "I" which is indicative of the degree of systemic inflammation by solving the equation:

"I=a(f)+b(h)+c"; wherein

"f" is the measured fibrinogen/fibrin level in the sample;

"h" is the determined hematocrit or hemoglobin value in the sample; and

"a", "b" and "c" are empirically derived constants; and g) correlating the numerical value of "I" with the degree of mammalian donor systemic inflammation.

2. The method of claim 1 wherein the blood sample is a sample of human blood, and wherein "h" is the determined hematocrit value; "a" equals 0.154; "b" equals −1.667; and "c" equals 42, and wherein the fibrinogen/fibrin level is expressed in mg/dl of the blood sample; and the hematocrit value is expressed as a volume percentage of packed red cells in the blood sample.

3. The method of claim 1 wherein the blood sample is a sample of human blood, and wherein "h" is the determined hemoglobin value; "a" equals 0.154; "b" equals −5.001; and "c" equals 42; and wherein the fibrinogen/fibrin level is expressed in mg/dl of the blood sample; and the hemoglobin value is expressed in gm/dl of the blood sample.

4. A method for determining the degree of donor systemic inflammation from a sample of donor anticoagulated human donor whole blood, said method comprising the steps of:

a) providing a transparent tube containing an elongated float;

b) drawing a sample of donor anticoagulated whole blood into said tube;

c) centrifuging the sample of whole blood in the tube;

d) measuring the amount of fibrinogen/fibrin in said blood sample;

e) determining a hematocrit value for the blood sample;

f) computing a number "I" which is indicative of the degree of systemic inflammation by solving the equation:

"I=a(f)+b(h)+c"; wherein

"f" is the measured fibrinogen/fibrin level in the sample;

"h" is the determined hematocrit value in the sample; and

"a" equals 0.154; "b" equals −1.667; and "c" equals 42, and wherein the fibrinogen/fibrin level is expressed in mg/dl of the blood sample; and the hematocrit value is expressed as a volume percentage of packed red cells in the blood sample; and g) correlating the numerical value of "I" with the degree of donor systemic mammalian inflammation.

5. A method for determining the degree of human donor systemic inflammation from a sample of anticoagulated donor whole blood, said method comprising the steps of:

a) providing a transparent tube containing an elongated float;

b) drawing a sample of donor anticoagulated whole blood into said tube;

c) centrifuging the sample of whole blood in the tube;

d) measuring the amount of fibrinogen/fibrin in said blood sample;

e) determining a hemoglobin value for the blood sample;

f) computing a number "I" which is indicative of the degree of systemic inflammation by solving the equation:

"I=a(f)+b(h)+c"; wherein

"f" is the measured fibrinogen/fibrin level in the sample;

"h" is the determined hemoglobin value in the sample; and

"a" equals 0.154; "b" equals −5.001; and "c" equals 42, and wherein the fibrinogen/fibrin level is expressed in mg/dl of the blood sample; and the hemoglobin value is expressed in gm/dl of the blood sample; and g) correlating the numerical value of "I" with the degree of donor systemic inflammation.

6. A method for determining the degree of donor systemic mammalian inflammation from mammalian donor anticoagulated whole blood, said method comprising the steps of:

a) measuring the amount of fibrinogen/fibrin in a sample of mammalian donor anticoagulated whole blood;

b) determining a hematocrit or hemoglobin value for said donor whole blood sample;

c) providing a computerized instrument which is programmed to compute a number "I" that is indicative of the degree of systemic inflammation by solving the equation:

"I=a(f)+b(h)+c"; wherein

"f" is the measured fibrinogen/fibrin level in the donor whole blood sample;

"h" is the determined hematocrit or hemoglobin value in the donor whole blood sample; and "a", "b" and "c" are empirically derived constants; and d) correlating the numerical value of "I" with the degree of donor systemic mammalian inflammation.

* * * * *